United States Patent [19]

Barrus

[11] Patent Number: 5,570,301
[45] Date of Patent: Oct. 29, 1996

[54] SYSTEM FOR UNENCUMBERED MEASUREMENT AND REPORTING OF BODY POSTURE

[75] Inventor: John W. Barrus, Lexington, Mass.

[73] Assignee: Mitsubishi Electric Information Technology Center America, Inc., Cambridge, Mass.

[21] Appl. No.: 275,496

[22] Filed: Jul. 15, 1994

[51] Int. Cl.⁶ ........................................... A61B 5/103
[52] U.S. Cl. ......................... 364/559; 73/172; 73/865.4; 364/550
[58] Field of Search ................ 33/511, 512; 73/172, 73/865.4; 297/217.1, 217.2, 217.3; 364/508, 550, 558, 559

[56] References Cited

U.S. PATENT DOCUMENTS

| | | | |
|---|---|---|---|
| 2,270,069 | 1/1942 | Martin | 33/512 |
| 5,060,174 | 10/1991 | Gross | 364/558 |
| 5,253,656 | 10/1993 | Rincoe et al. | 73/172 X |
| 5,369,601 | 11/1994 | Tannenbaum | 364/558 |

*Primary Examiner*—Edward R. Cosimano
*Attorney, Agent, or Firm*—Robert K. Tendler, Esq.

[57] ABSTRACT

A system for unencumbered measurement of body posture or attitude utilizes non-encumbering force or proximity sensors to monitor an individual, where the individual need not be aware of the presence or action of the sensors. Outputs from these sensors are analyzed to infer body posture or attitude. In one embodiment, a set of sensors is attached to a chair, or other surroundings such as the floor, at locations where a person may be in contact with or in close proximity to one or more of the sensors or where movement of the chair could be detected. Each sensor has an output which provides a signal indicative of a response of the sensor to forces exerted by or motions of the individual. The outputs of the sensors are processed to estimate the body posture of the individual.

20 Claims, 5 Drawing Sheets

SYSTEM FOR UNENCUMBERED MEASUREMENT AND REPORTING OF BODY POSTURE

FIELD OF THE INVENTION

This invention is related to measurement and reporting of body posture or attitude using non-encumbering sensors and more particularly to computer animation and input devices for controlling display of animated characters.

BACKGROUND OF THE INVENTION

Video games often include input devices which enable a user to control the position or orientation of an animated character. One problem with typical input devices used with video games is that the body movements needed to use a joystick, trackball, mouse or keyboard input to cause an animated character to move on a video display have no direct or intuitive relationship with the resulting movement of the animated character. For example, a user may move his hand forward or press a key to cause an animated figure to walk. These systems, because they are not intuitive, are typically difficult to learn.

Recently, animated characters have also been used in video-conferencing systems. In such video-conferencing systems, a user controls an animated character so that its posture reflects the mood desired by the individual. In particular, such an animated video conferencing system is described in U.S. Patent application Ser. No. 08/169,163, filed Dec. 17, 1993, now U.S. Pat. No. 5,347,306 issued on Sept. 13, 1994, which is commonly assigned with this application to Mitsubishi Electronic Research Laboratories of Cambridge, Mass.. This system also includes an input device which a user wears to provide indications of the positions of parts of the body. Individuals may control movement of an animated character with their own body movements. That is, an individual could move an arm to cause the arm of the animated character to move in a similar manner. There are a variety of these kinds of devices.

One type of such device is the ADL-1, from Shooting Star Technology, of Burnaby, British Columbia, Canada, which is a six degree-of-freedom mechanical head-tracking device. A similar device, available from SimGraphics Engineering in South Pasadena, Calif., mechanically tracks several locations on the wearer's face and displays an animated face whose lips and expressions move in synchronization with those of the wearer.

There are suits or other types of clothing that can be worn by a user to indicate the motions of the joints of the user for body tracking. Examples of these are the CyberGlove, CyberArm, CyberVest, and CyberSuit, all part of a product line called CyberWear body instrument garments from Virtual Technologies, of Stanford, Calif.. A magnetic tracker called FasTrak is available from Polhemus, Inc., of Colchester, Vt., which gives a computer six coordinates that specify the location and orientation of a hand. There are also video tracking systems where the user wears a series of reflective markers or light emitting diodes (LEDs) which are tracked using video cameras.

These devices generally have significant drawbacks. The first is that users are encumbered by having wired sensors directly attached to them or clothing and therefore have limited motion. For example, with one such device, a user wears a helmet and the helmet is attached to a wall via an articulated arm. Users cannot freely walk around or move their hands and head without running the risk of hitting wires, and possibly disconnecting them from the computer. The clothing usually requires assistance to be put on and taken off, and may have to be individually tailored.

In an attempt to avoid these drawbacks, optical systems which perform a variety of image recognition tasks, such as object and motion recognition, eye tracking, gesture recognition, etc., have been used. These systems perform a task similar to that performed by the body language researcher, though in an automated manner. A significant drawback with image recognition systems is that they require computationally intensive processing by a powerful computer, and are therefore expensive. More importantly, the time required to perform appropriate computations results in unacceptable latency. Thus, animated characters controlled by the input device do not track actual movements of the individual, resulting in inadequate performance.

Experts have filmed and video-taped body motions of people in interview situations and everyday communication. They use these recordings for carefully watching and noting body motion to determine how "body language" is used as an additional communication channel. These experts, in a field called kinesics, have created a written language, similar to musical notation, to record body movements in a way that completely communicates the motion of the participant to others in their field. In the past, the only way to record the body motion in writing was to view the film or video tape over and over, taking careful notes of the motions and posture of the participant.

For the purposes of providing further background information, U.S. Pat. No. 5,060,174 describes a chair which is adapted to provide pressure profiles from when an individual is seated in the chair. This system is not used to infer posture, but rather to evaluate the load bearing quality of the seat.

SUMMARY OF THE INVENTION

The invention overcomes many of the disadvantages of the prior art by monitoring forces exerted by or motions of an individual in an environment, e.g., furniture, the floor, or other surroundings, using non-encumbering sensors such that the individual is neither encumbered by wires or other sensors attached to them or their clothing. Non-encumbering means neither worn nor attached to an individual or an individual's clothing. The individual need not be aware of the presence or activity of the sensors. The posture or positional attitude of the whole body of the individual is then inferred from the detected forces and motions and this inferred posture is reported.

This system allows some of the information collected in body language studies to be recorded directly from the motions of an individual in natural surroundings, such as while sitting in a specially modified chair. In this way, "body language" can be communicated simply and effectively over a low-bandwidth computer network and used as an additional channel for computer-based communication among people.

The reported, inferred posture can be used in many applications. An animated figure can be controlled to mimic the inferred posture, such as in a video conferencing system or in a video game, such as by controlling the movement of a simulated luge. Other computer systems could be controlled, such as music creation, etc. Activity of an individual can be monitored or reported, e.g., whether a user is sitting, reclining, not in a chair, etc. Additionally, body language studies could be performed.

Accordingly, one aspect of the present invention is a computer system for non-encumbered measurement of positional attitude of an individual. This system includes a device adapted to be used by the individual when operating the computer system. A plurality of sensors are associated with the device, and each sensor has an output which provides a signal indicative of a response of the sensor to the individual using the device. A positional attitude of the individual relating to the device is estimated from the signals output by said plurality of sensors.

Another aspect of the invention is a system for non-encumbered measurement of body posture of an individual. This system monitors forces an individual exerts on an environment in a non-encumbering manner and processes the monitored forces to infer the body posture of the individual.

Another aspect of the invention is a system for non-encumbered measurement of body posture of an individual which monitors motions of an individual in an environment in a non-encumbering manner. The monitored motions are processed to infer the body posture of the individual.

In a preferred embodiment of the invention, an animated image of the individual is displayed on said computer display in a positional attitude which mimics the estimated positional attitude. The device used by the individual may be furniture, such as a chair. The device may also include a floor to which sensors are attached. The sensors may be force or pressure sensors, strain gauges, positional encoders or proximity sensors.

Positional attitude may be estimated by comparing the outputs of the sensors to pre-determined outputs of the sensors corresponding to a plurality of pre-determined postures. Positional attitude may also be estimated using a kinematic or dynamic model of the human body and by processing the sensor inputs to identify a posture of the human body in which the body is in equilibrium according to the model.

The predetermined postures may be defined by directing the individual to assume each of a plurality of selected postures. The status of the outputs of said sensors in response to each of the selected posture assumed by the individual is then stored.

BRIEF DESCRIPTION OF THE DRAWING

These and other features of the subject invention will be better understood in connection with the Detailed Description taken in conjunction with the Drawing of which.

FIG. is a perspective view of an individual and an animated character mimicking a first posture of the individual.

DETAILED DESCRIPTION

Figure 1:
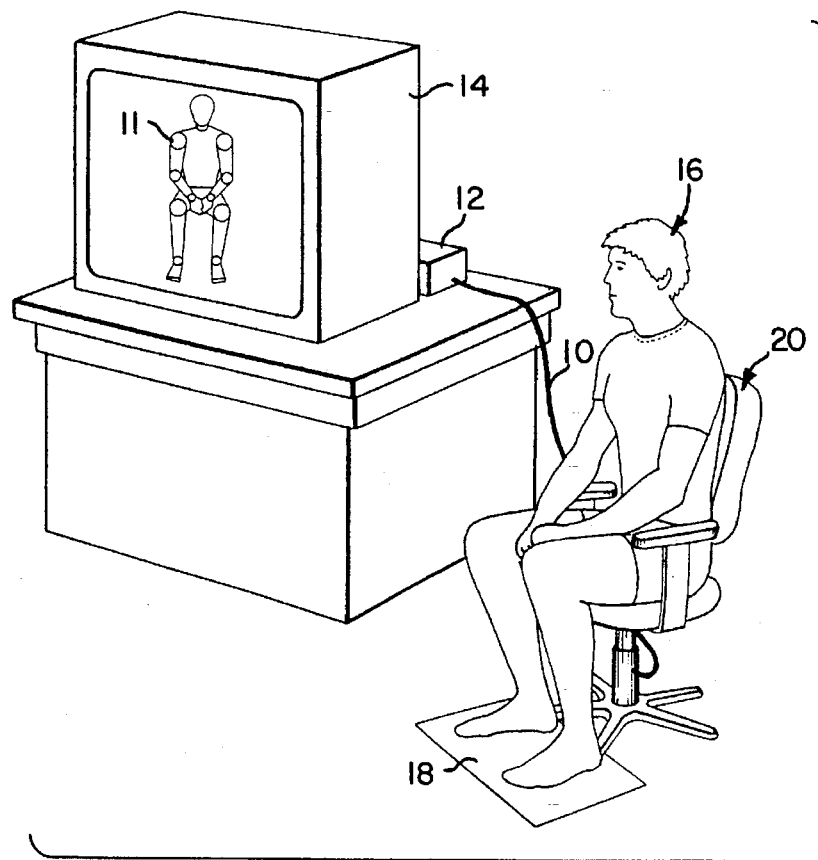

FIG. 1 illustrates how the present invention is preferably used. FIG. 1 shows a chair 20 and a floor pad 18 on which an individual 16 is seated. A computer display 14, connected to a computer 12, is connected to the chair via cable 10. The chair includes some sensors which detect the effect that the individual 16 has on the surrounding environment, such as the chair 20 and floor pad 18. The sensors, which are not shown in this figure but are discussed below, are not to be attached to the individual 16, but rather to the chair and floor. Thus, the individual is are not encumbered and monitoring of the individual using the sensors is performed in a non-encumbering manner. Also, the sensors detect the forces or motion of the individual in a manner such that the user need not be aware of the presence or activity of the sensors.

The computer 12 processes the outputs from the sensors, in a manner to be described below, so as to infer the body posture or positional attitude of the person. This body posture is then reported. It can be reported by using a representative image of the posture, by a text string describing the posture or by a set of joint angles describing the orientation of certain joints of the individual's body.

The reported posture can be used in many ways. For example, an animated character 11 may be displayed on display 14 such that the posture of the animated character mimics that of the individual 16. Controlling a display of an animated character involves techniques which are well known in this art Given a desired posture of the animated character, such as an indication of the back, arm, head and leg positions, the character can be readily displayed using conventional techniques.

Figure 2:
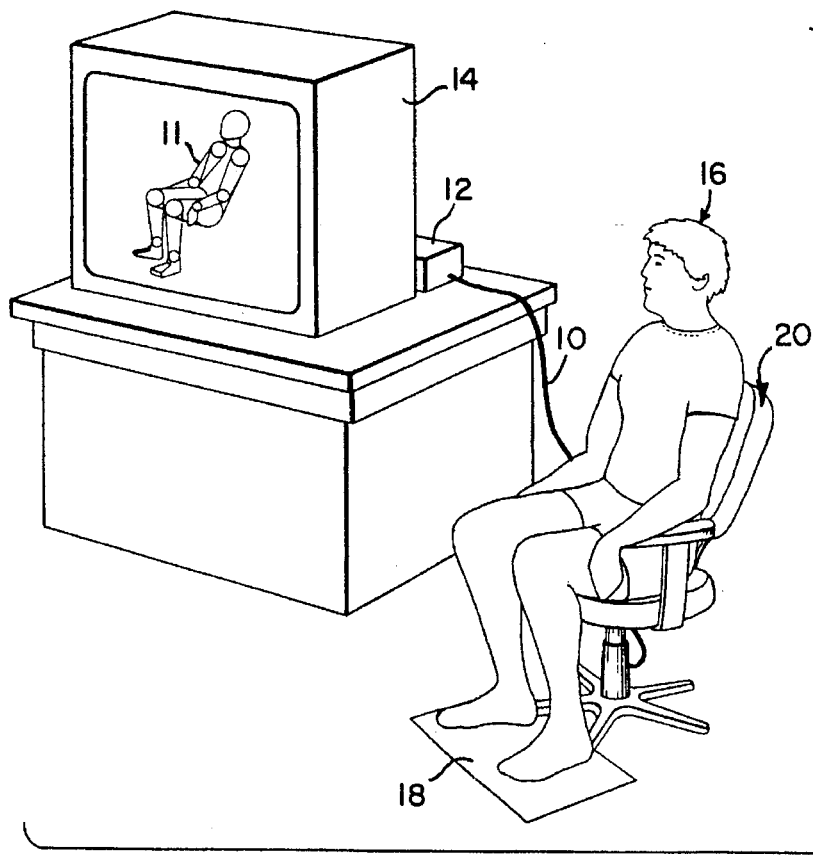
FIG. 2 is a perspective view of an individual and an animated character mimicking a second posture of the individual.

When a user moves, such as shown in FIG. 2, e.g., by reclining, such that the back of the individual 16 touches the back of the chair 20, and by rotating, the output of the sensors becomes different and thus a new posture may be inferred. This new posture can be reported and, for example, the position of the animated character on the screen may change.

Figure 3:
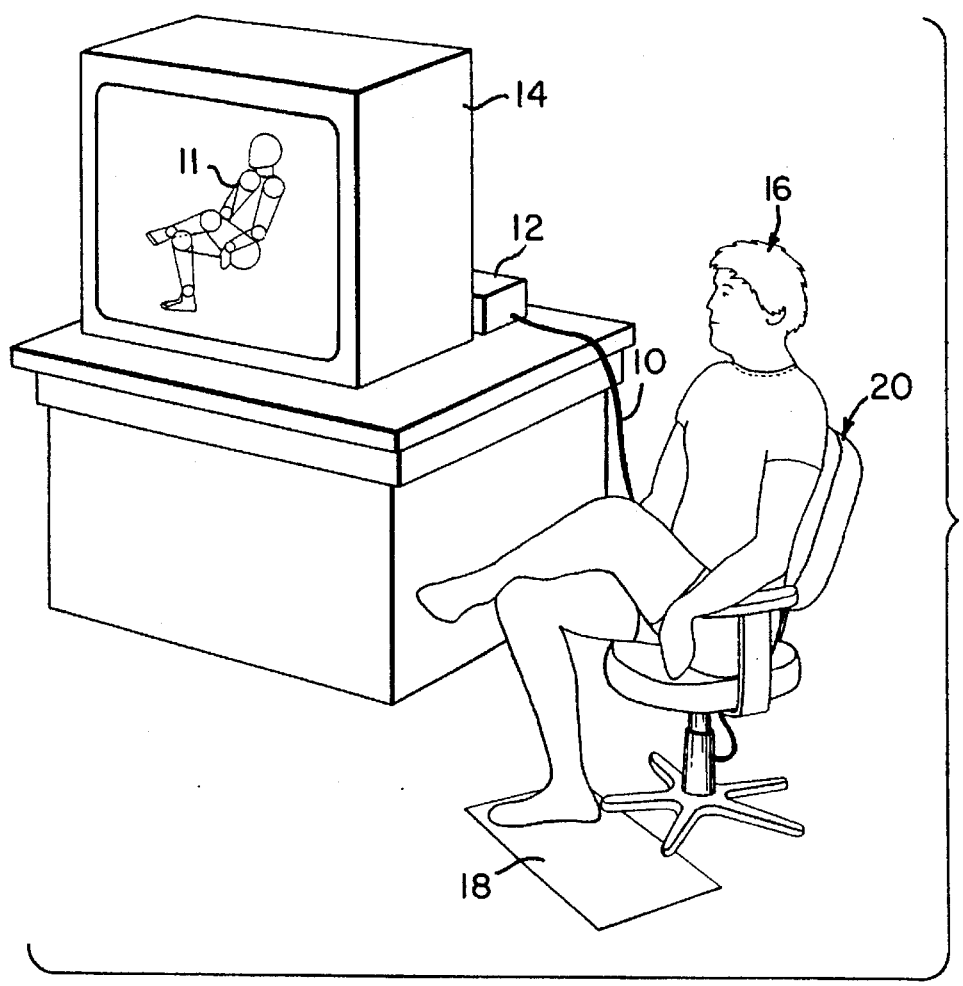
FIG. 3 is a perspective view of an individual and an animated character mimicking a third posture of the individual.

The individual 16 may even cross legs, such as shown in FIG. 3, and the sensor outputs again change. A new posture can then be inferred and reported. Accordingly, the animated character may mimic this posture as well, as shown in FIG. 3.

A significant benefit of this system is that the user is not encumbered by the monitoring of the user by the computer. In other words, this monitoring is performed in a transparent manner, i.e., without the user being aware of it. A user of this system, for example, in a video conferencing application, can readily use this system without the need for assistance to put on special clothing, and can readily move about as desired during a video conferencing session. Also, this system is less expensive than imaging technology. Its simple use and non-encumbered, transparent nature, thus provides significant improvements over the prior art.

Figure 4:
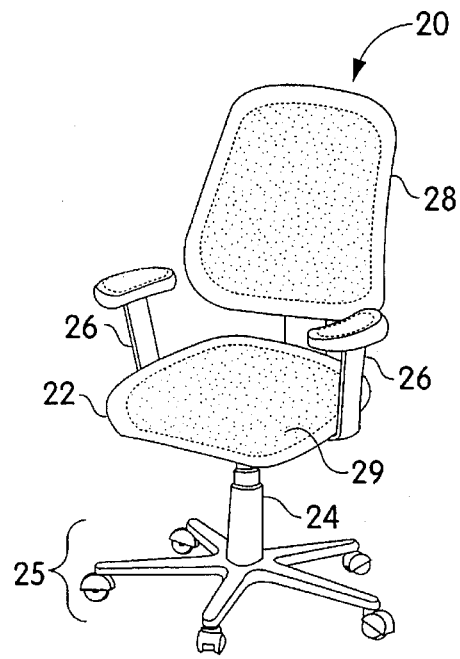
FIG. 4 shows a chair having a plurality of force or proximity sensors attached thereto.

Referring now to FIG. 4, a chair 20 is illustrated which is suitable for use in connection with the present invention. As used in this application, the term "chair" defines a piece of furniture which has a substantially horizontal surface upon which a individual may sit. For example, chair 20 in FIG. 4 has a horizontal support member 22. In a chair, the horizontal support member is supported by one or more legs. The chair 20 in FIG. 4 is supported by one leg 24 with a five-spoke base 25. A chair may also have arms such as shown at 26 in FIG. 4 and possibly a back 28. Some chairs are constructed so as to have a variety of positions, such as rotation or reclining. Such chairs can also be adapted for use with the present invention. As indicated in FIG. 4, the surfaces of the chair 20 which a individual may contact while sitting (as indicated by the shaded portion 29) are equipped with sensors, which will be described in more detail below. Sensors may also be attached to movable portions of the chair.

The sensors preferably are force sensors, but may also be strain gauges, proximity sensors or position encoders attached to movable portions of the chair. Sensors that detect motion and rotation of chair parts are usually called encoders. Sensors that detect forces between that body and the chair are pressure sensors or force sensors. Sensors which detect motion near, but not touching, the sensor are proximity sensors. Any combination of these sensors may be used. A chair with pressure sensors is described in U.S. Pat. No. 5,060,174, but does not describe using the output of the sensors to infer body posture.

Figure 5:
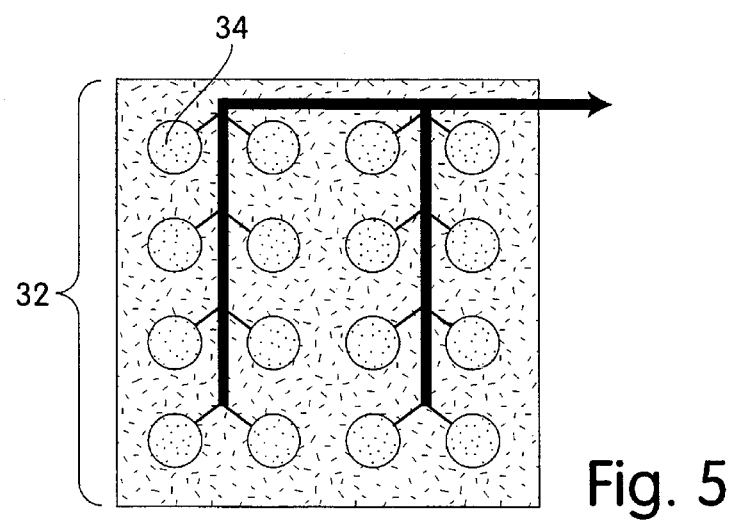
FIG. 5 is a schematic diagram of a sensor in an array as may be used in connection with the present invention.
Figure 6:
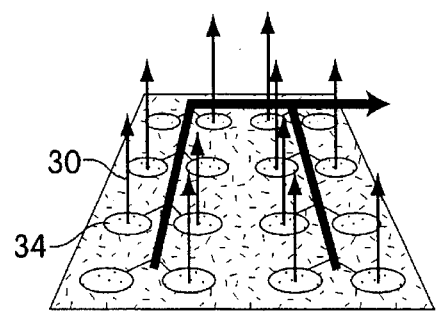
FIG. 6 is an illustration of the magnitude of the output produced by each force sensor when force is applied to the sensor array.

As can be seen in FIG. 5, a sensor array 32 is shown which may be used in the various locations identified by shaded regions in FIG. 5. In one embodiment, each sensor 34 is comprised of layers of material whose electrical resistance changes with an increase in pressure applied to the sensor. This dependence on pressure is illustrated in FIG. 6 where the length of an arrow 30 is related to the amount of force applied to the sensor 34. Arrays of these sensors provide multiple output signals which can then be input to the computer. Suitable sensors for this purpose are force sensing resistors (FSRs) manufactured by Interlink Electronics of Camarillo, Calif.. Alternatively, proximity sensors, which indicate a distance from the sensor to an object, may be used. Such sensors have been developed by the Media Lab of the Massachusetts Institute of Technology, in Cambridge, Mass..

Figure 7A:
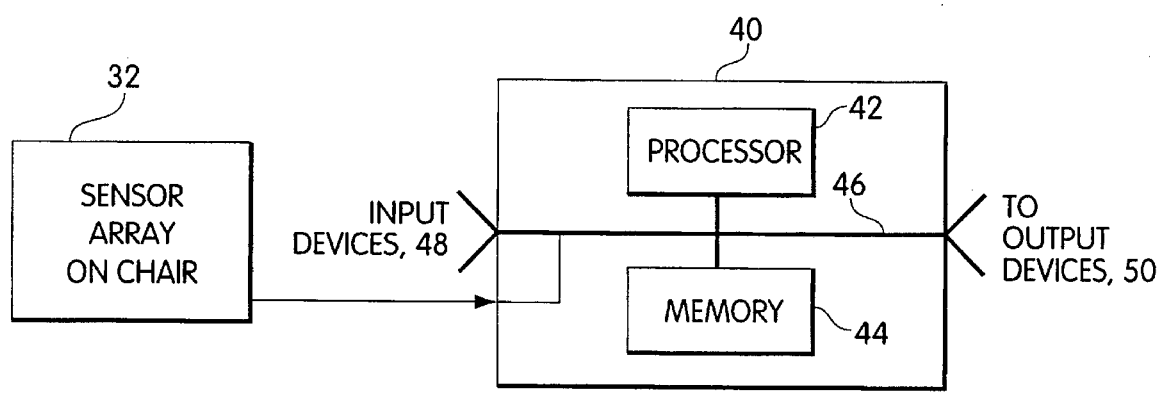
FIG. 7a is a block diagram of a computer system suitable for utilizing the present invention.

A suitable computer system for processing these input signals is shown in FIG. 7a. The computer system 40 includes a processor 42 connected to a memory 44 via a bus 46. Input devices 48 may be attached to this bus 46, as well as output devices 50. The processor 42 operates under the control of computer instructions, typically stored in the memory 44, so as to provide useful operations on data and other input received through the input devices.

Figure 7B:
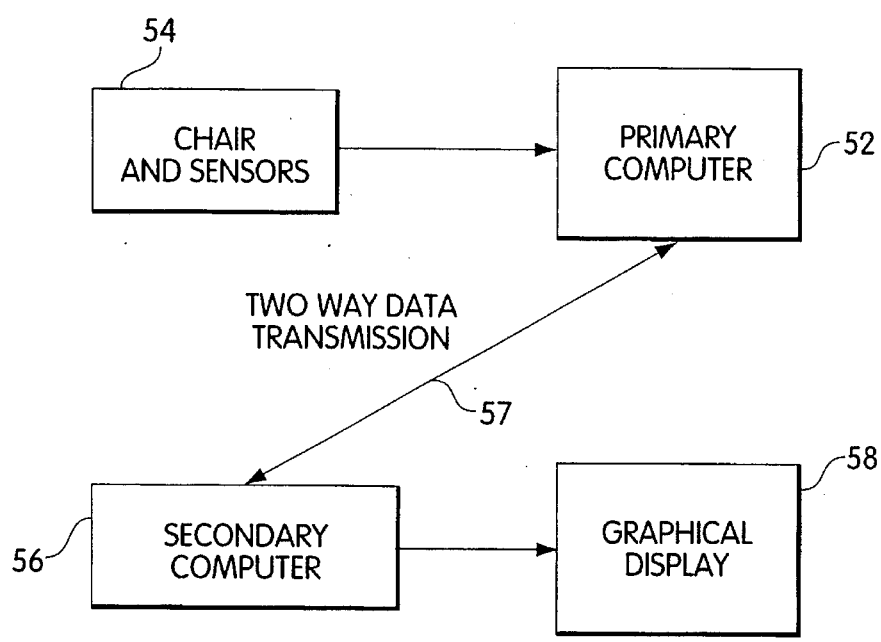
FIG. 7b is a block diagram of a second computer system in which a first computer is attached to a chair and a second computer processes outputs from the first computer to infer posture.

In a particular embodiment, the computer system has a construction as shown in FIG. 7b. This computer system has two computers. A primary computer 52, typically attached to the sensors on the chair as indicated at 54, converts outputs from the sensors from analog to digital form, such as a digital representation of an integer or floating point value, and transmits the digital representation to a secondary computer 56 over a two-way data transmission link 57. The two-way transmission link may be, but is not limited to, a serial connection, a parallel connection, a local area network, or radio frequency or other wireless transmission medium. The secondary computer 56 has an input adapted to read data from the primary computer 52 and infer and report body posture. This secondary computer 56 typically includes a graphical display 58 if the body posture is used for animation or visual reporting of the posture. A suitable secondary computer 56 is the Indigo computer available from Silicon Graphics, Inc., of Mountain View, Calif..

The primary computer 56 includes one or more multiplexed analog-to-digital converters to read and convert sensor outputs. In the preferred embodiment, a converter is controlled using a small microcontroller with a random-access memory for storing the digitized sensor data and a read-only memory for program storage. A suitable microcontroller is the 68HC11 series microcontroller available from Motorola, or the 8051 series microcontroller available from Intel.

A personal computer with a data acquisition system can also be used to implement both the primary and secondary computers 52 and 56. For example, computers available from Gateway 2000 of Souix City, Iowa, can be used with data acquisition boards from Kiethley/Metrabyte of Taunton, Mass.. However, it is preferable to have a separate computer on the chair or with the sensors for managing data acquisition and for communicating it to another computer which will process the data.

Figure 8:
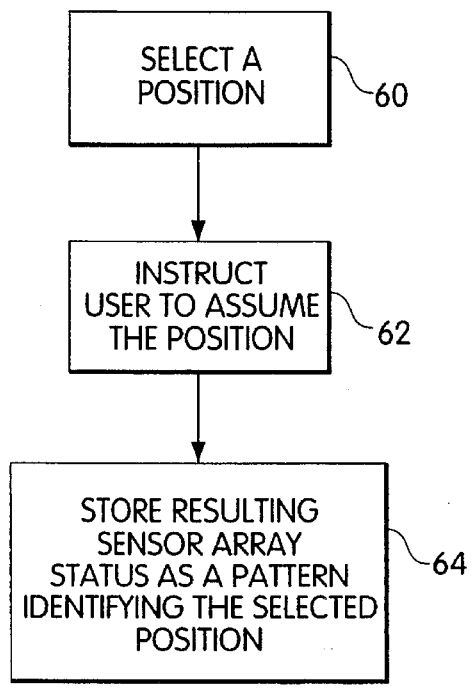
FIG. 8 is a flow chart describing how the input device of the present invention may be calibrated.

The operation of a computer system to utilize the posture input device described above to identify the posture of an individual using the chair will now be described in connection with the flow chart of FIG. 8. A chair so equipped with sensors is preferably calibrated before use. The calibration procedure may take many forms; however, the simplest form of calibration is to select a small set of predetermined possible positions of the user of the chair, as indicated at step 60. For each of the selected positions, the computer instructs the user to assume that position in the chair in step 62, perhaps by displaying an animated figure in that position graphically. After the user assumes that position, the computer system requests and stores the status of the sensors as a representation of that position, as indicated in step 64.

As to the predetermined postures, because the weight and extent of each person who might use the chair varies, the computer should correlate the position of the participant with the values of the sensors. There are two possible methods for calibrating the chair to assume or mimic the posture of the sitter. One method tries to mimic bocy attitude by calculating the most likely position of several different points on the body and, using constraints and inverse kinematic solvers, find the most likely joint angles of the body. An animated body displayed on the computer could take an infinite number of poses based on the conversion of the sensor outputs to joint angles.

Frequently, such complex input-output mapping is accomplished using a neural network. The neural network is trained by specifying what the outputs should be for a given set of inputs. Once enough examples have been given, the neural network can adjust the body correctly, even for unfamiliar input values.

Figure 9:
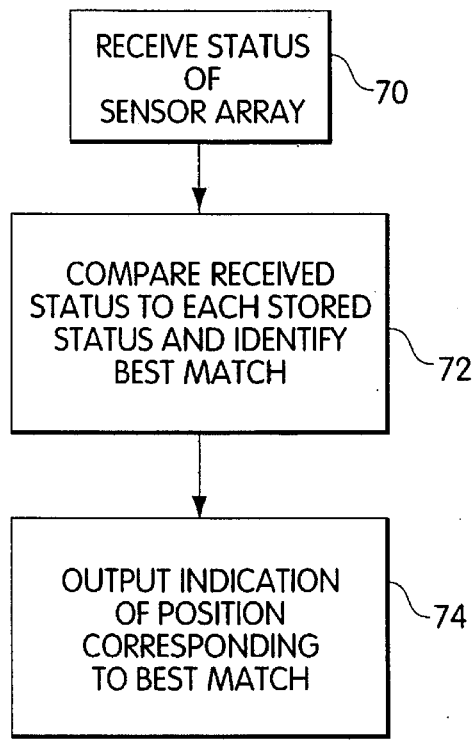
FIG. 9 is a flow chart describing how inputs from the input device in accordance with the present invention are processed after calibration.

After calibration, such as by a procedure described in connection with FIG. 9, the posture input device is ready for use. To use the posture input device, the primary computer periodically sends the secondary computer the status of the sensors in the sensor array as indicated in step 70 whenever the status of the sensors changes. The secondary computer at 72 then compares the received status to the status of each of the predetermined positions selected during calibration. When the computer identifies the best match as illustrated at 74, the best match is selected as the likely or estimated position of the individual using the chair. These steps of comparison or identifying a best match can be performed in many ways known to those of skill in the field of digital computer programming. For example, one way to determine the best match is to assume that n sensor values describe a point in n-dimensional space. For instance, if there are three values, each value represents one axis in three dimensions, e.g., x, y and z. Then, the closest match is the predetermined posture having values which are closest in distance (or most similar) to the values input from the sensors, where distance may be measured using any distance (or similarity) metric, such as Euclidean distance. In n dimensions, the n-dimensional distance is calculated in a manner similar to the 3-dimensional case. The distance from the measured point to all of the predetermined points is calculated and the predetermined point with the smallest distance is selected.

The secondary computer 56 can also estimate a user's position by using a kinematic or dynamic model of the human body. Such models are known in the art. For example, one is described in *Simulating Humans* (New York: Oxford University Press, 1993), by N. B. Badler et al. A model can be used in combination with the measured forces to determine the user's position according to the principle that all external forces on the human body must add up to zero. The input from the posture input device can be used for a variety of applications, In particular, it is especially useful for use in an animated video conferencing system such as described in U.S. Patent application Ser. No. 08/169,163, filed Dec. 17, 1993 now U.S. Pat. No. 5,347,306 issued on Sept. 13, 1994, which is commonly assigned with this application to Mitsubishi Electronic Research Laboratories of Cambridge, Mass.. In such an application, the posture, gesture or action of a individual may be displayed.

Other devices already instrumented in the environment of the individual may be used to determine additional information about body position. For instance, if the individual is in front of a computer, the motion of a joystick or mouse indicates motion of the user's hand in most cases. Motion of keys on the keyboard also provides cues as to the position of the individual's fingers. Finding an individual's posture is easier with the additional information these devices provide.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art. For example, sensors may be attached to a floor, carpet or other environmental surroundings to detect forces a individual exerts on the environment without attaching wires to the individual or a individual's clothing. By using kinematic and dynamic models of the human body and the principles of equilibrium discussed above, a individual's position can be estimated. These and other modifications are contemplated as falling within the scope of the invention as defined by the appended claims.

What is claimed is:

1. A computer system for non-encumbered measurement of positional attitude of an individual, comprising:

a non-encumbering device adapted to be used by said individual when operating said computer system;

a plurality of sensors associated with said device, each sensor having an output which provides a signal indicative of a response of the sensor to the individual using said device;

means for estimating a positional attitude of the individual relating to said device from the signals output by said plurality of sensors; and, means for displaying an animated image of the individual on said computer display in a positional attitude which mimics the estimated positional attitude of the individual.

2. The system of claim 1 wherein said device includes a floor and said plurality of sensors are attached to the floor.

3. The system of claim 1 wherein said estimating means includes means for comparing the outputs of the sensors to pre-determined outputs of said sensors corresponding to a plurality of pre-determined postures.

4. The method of claim 1 wherein estimating means includes a kinematic model of the human body which processes the sensor inputs to identify a posture of the human body in which the body is in equilibrium.

5. The system of claim 1 wherein said sensors are force sensitive resistors.

6. The system of claim 1 wherein said sensors are proximity sensors.

7. The system of claim 1, wherein said estimating means includes:

means for selecting a plurality of pre-determined postures;

means for directing the individual to assume each of the selected postures; and means for storing the status of the outputs of said sensors in response to each of the selected postures assumed by the individual.

8. The system of claim 1 wherein said device includes a chair.

9. The system of claim 1 wherein estimating means includes a dynamic model of the human body which processes the sensor inputs to identify a posture of the human body in which the body is in equilibrium.

10. A system for non-encumbered measurement of body posture of an individual, comprising:

means for monitoring forces an individual exerts on an environment in a non-encumbering manner;

means for processing the monitored forces to infer the body posture of the individual; and, means for displaying an animated character on a computer display such that the animated character mimics the body posture of the individual.

11. The system of claim 10, wherein the means for monitoring includes an plurality of force sensing resistors.

12. The system of claim 11, wherein the force sensing resistors are attached to a chair, at locations where a person may be in contact with one or more of the sensors.

13. The system of claim 11, wherein the force sensing resistors are attached to a floor, at locations where a person may be in contact with one or more of the sensors.

14. A system for non-encumbered measurement of body posture of an individual, comprising:

means for monitoring motions of an individual in an environment in a non-encumbering manner;

means for processing the monitored motions to infer the body posture of the individual; and, means for displaying an animated character on a computer display such that the animated character mimics the body posture of the individual.

15. The system of claim 14, wherein the means for monitoring includes an plurality of proximity sensors.

16. The system of claim 15, wherein the proximity sensors are attached to a chair, at locations where a person may be in close proximity to one or more of the sensors.

17. The system of claim 15, wherein the proximity sensors are attached to a floor, at locations where a person may be in close proximity to one or more of the sensors.

18. A computer system for non-encumbered measurement of positional attitude of an individual comprising:

a non-encumbered device adapted to be used by said individual in operating said computer system;

a plurality of sensors associated with said device, each sensor having an output which provides a signal indicative of a response of a sensor to the individual using said device; and, means for estimating a positional attitude of the individual relating to said device from the signals output by said plurality of sensors, said estimating means including means for comparing the outputs of the sensors to predetermined of said sensors corresponding to a plurality of predetermined postures.

19. A computer system for non-encumbered measurement of positional attitude of an individual comprising:

a non-encumbered device adapted to be used by said individual in operating said computer system;

a plurality of sensors associated with said device, each sensor having an output which provides a signal indicative of a response of a sensor to the individual using said device; and, means for estimating a positional attitude of the individual relating to said device from the signals output by said plurality of sensors, said estimating means including means for selecting a plurality of predetermined postures, means for directing the individual to assume each of the selected postures and means for storing the status of the outputs of said sensors in response to each of the select postures assumed by the individual.

20. A computer system for non-encumbered measurement of positional attitude of an individual comprising:

a non-encumbered device adapted to be used by said individual in operating said computer system;

a plurality of sensors associated with said device, each sensor having an output which provides a signal indicative of a response of a sensor to the individual using said device; and, means for estimating a positional attitude of the individual relating to said device from the signals output by said plurality of sensors, said estimating means including a dynamic model of human body which processes the sensor inputs to identify a posture of the human body in which the body is in equilibrium.

* * * * *